US009958466B2

(12) United States Patent
Dalbert et al.

(10) Patent No.: US 9,958,466 B2
(45) Date of Patent: May 1, 2018

(54) REFLEX TESTING OF SAMPLES USING RESIDUAL MATERIALS FROM A PRIOR TEST

(71) Applicant: BECTON, DICKINSON AND COMPANY, Franklin Lakes, NJ (US)

(72) Inventors: Celine Roger Dalbert, Quebec (CA); Joel Daniel Krayer, Baltimore, MD (US); Adam Bruce Steel, Fallston, MD (US); Denis Roy, Quebec (CA)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days. days.

(21) Appl. No.: 14/510,875

(22) Filed: Oct. 9, 2014

(65) Prior Publication Data

US 2015/0024375 A1    Jan. 22, 2015

Related U.S. Application Data

(63) Continuation of application No. PCT/US2013/031072, filed on Mar. 13, 2013.

(60) Provisional application No. 61/624,198, filed on Apr. 13, 2012.

(51) Int. Cl.
  *G01N 35/00* (2006.01)
  *C12Q 1/68* (2018.01)
  *G01N 35/04* (2006.01)

(52) U.S. Cl.
  CPC ....... *G01N 35/00603* (2013.01); *C12Q 1/689* (2013.01); *C12Q 2600/156* (2013.01); *G01N 2035/0436* (2013.01); *Y10T 436/11* (2015.01)

(58) Field of Classification Search
  CPC .. G01N 31/22; G01N 35/00; G01N 33/56938; C12Q 1/68; C12Q 3/00
  See application file for complete search history.

(56) References Cited

U.S. PATENT DOCUMENTS

| | | | |
|---|---|---|---|
| 3,890,203 A | 6/1975 | Mehl | |
| 3,901,765 A | 8/1975 | Mehl | |
| 3,904,482 A | 9/1975 | Mehl | |
| 3,917,455 A | 11/1975 | Bak et al. | |
| 4,618,576 A | 10/1986 | Rosenstein et al. | |
| 4,693,972 A | 9/1987 | Mansour et al. | |
| 5,084,005 A | 1/1992 | Kachigian | |
| 5,091,316 A | 2/1992 | Monthony et al. | |
| 5,646,049 A | 7/1997 | Tayi | |
| 5,776,694 A | 7/1998 | Sheiness et al. | |
| 6,409,968 B1 | 6/2002 | Takahashi | |
| 6,617,170 B2 | 9/2003 | Augello et al. | |
| 7,405,073 B2 * | 7/2008 | Tilles ...................... | B01L 3/502 422/50 |
| 7,662,562 B2 | 2/2010 | Hellyer et al. | |
| D655,424 S | 3/2012 | Castanon et al. | |
| 8,420,320 B2 | 4/2013 | Hellyer et al. | |
| 8,603,769 B2 | 12/2013 | Feng et al. | |
| 2002/0146677 A1 | 10/2002 | Augello et al. | |
| 2003/0022392 A1 | 1/2003 | Hudak | |
| 2004/0063197 A1* | 4/2004 | Tilles ...................... | B01L 3/502 435/287.2 |
| 2004/0176705 A1 | 9/2004 | Stevens et al. | |
| 2005/0013737 A1 | 1/2005 | Chow et al. | |
| 2006/0004526 A1* | 1/2006 | Hadd ...................... | G06F 19/26 702/20 |
| 2006/0127924 A1 | 6/2006 | Hellyer et al. | |
| 2006/0246423 A1 | 11/2006 | Adelson et al. | |
| 2008/0124738 A1* | 5/2008 | Green ...................... | C12Q 1/04 435/7.1 |
| 2008/0196517 A1 | 8/2008 | Harvey et al. | |
| 2008/0280296 A1 | 11/2008 | Chen et al. | |
| 2009/0098527 A1 | 4/2009 | Fischer et al. | |
| 2009/0123909 A1 | 5/2009 | Pourmand et al. | |
| 2009/0130745 A1 | 5/2009 | Williams et al. | |
| 2009/0137047 A1* | 5/2009 | Regan ...................... | G01N 35/04 436/48 |
| 2009/0203022 A1* | 8/2009 | Zenhausern ......... | C12Q 1/6848 435/6.12 |
| 2009/0233309 A1 | 9/2009 | Fischer et al. | |
| 2009/0291449 A1 | 11/2009 | Knapp, Jr. et al. | |
| 2009/0306230 A1 | 12/2009 | Semikhodskii et al. | |
| 2009/0312285 A1 | 12/2009 | Fischer et al. | |
| 2010/0009343 A1 | 1/2010 | Fischer et al. | |
| 2010/0311607 A1 | 12/2010 | Hellyer et al. | |
| 2011/0022327 A1 | 1/2011 | Busenhart et al. | |
| 2011/0158865 A1 | 6/2011 | Miller et al. | |
| 2011/0159578 A1 | 6/2011 | Godsey et al. | |

(Continued)

FOREIGN PATENT DOCUMENTS

| | | |
|---|---|---|
| EP | 0143329 A2 | 6/1985 |
| EP | 0703456 B1 | 8/2003 |

(Continued)

OTHER PUBLICATIONS

Perez-Roth et al, Multiplex PCR for Simultaneous Identification of *Staphylococcus aureus* and Detection of Methicillin and Mupirocin Resistance, 2011, Journal of Clinical Microbiology, 39, 4037-4041.*
MagNA® Pure LC RNA Isolation Tissue Lysis Buffer—Refill; Package Insert; Roche, Version 1; Printed Jun. 2003; pp. 2.
International Preliminary Report on Patentability dated Oct. 23, 2014 for Application No. PCT/US2013/031072, filed Mar. 13, 2013.
Beck et al., "Development of a Rapid Automated Influenza A, Influenza B, and Respiratory Syncytial Virus A/B Multiples Real-Time RT-PCR Assay and Its Use during the 2009 H1N1 Swin-Origin Influenza Virus Epidemic in Milwaukee, Wisconsin", J Mol Diagnos. (Jan. 2010) 12(1).
Booth et al., "Comparison of two rapid influenza A/B test kits with reference methods showing high specificity and sensitivity for influenza A infection", J Med Virol. (Jan. 1, 2006) 78(5):619-622.

(Continued)

*Primary Examiner* — Narayan Bhat
(74) *Attorney, Agent, or Firm* — Knobbe Martens Olson & Bear LLP

(57) ABSTRACT

Embodiments disclosed herein relate to methods and systems for performing automated assays, and particularly to performing sequential assays on a sample on an automated instrument.

25 Claims, 3 Drawing Sheets

(56) References Cited

U.S. PATENT DOCUMENTS

| | | | |
|---|---|---|---|
| 2011/0200991 A1* | 8/2011 | Hansen | B01L 3/50855 435/6.1 |
| 2011/0262919 A1 | 10/2011 | Tajima | |
| 2012/0003710 A1 | 1/2012 | Leinweber et al. | |
| 2013/0089886 A1 | 4/2013 | Feng et al. | |
| 2013/0183769 A1 | 7/2013 | Tajima | |
| 2013/0216998 A1 | 8/2013 | Carrino et al. | |
| 2014/0329705 A1 | 11/2014 | Wong et al. | |

FOREIGN PATENT DOCUMENTS

| | | |
|---|---|---|
| JP | H 0266461 A | 3/1990 |
| JP | H08-94636 A | 4/1996 |
| JP | H08-506421 A | 7/1996 |
| JP | 2000-146987 A | 5/2000 |
| JP | 2004-534731 | 11/2004 |
| JP | 2006-084351 | 3/2006 |
| JP | 2006125868 A | 5/2006 |
| JP | 2008-164403 | 7/2008 |
| JP | 2009-523458 | 6/2009 |
| JP | 2010054232 A | 3/2010 |
| JP | 2010533490 A | 10/2010 |
| JP | 2011-039046 A | 2/2011 |
| SU | 677682 A3 | 7/1979 |
| WO | WO 2004/078233 A2 | 9/2004 |
| WO | WO 2006/116010 A | 11/2006 |
| WO | WO 2009/082747 * | 7/2009 |
| WO | WO 2009/082747 A | 7/2009 |
| WO | WO 2010/039917 A | 4/2010 |
| WO | WO 2010/064628 | 6/2010 |
| WO | WO 2010/074265 A | 7/2010 |
| WO | WO 2012/012527 A2 | 1/2012 |
| WO | WO 2012/036296 A | 3/2012 |

OTHER PUBLICATIONS

Das et al., "Development of an internal positive control for rapid diagnosis of avian influenza virus infections by real-time reverse transcription-PCR with lyophilized reagents", J Clin Microbiol. (Sep. 2006) 44(9):3065-3073.

Fearson, Margaret, "The laboratory diagnosis of HIV infections", Can J Infect Dis Med Microbiol. (Jan. 2005) 16(1),26-30.

Foo et al., "Laboratory test performance in young adults during influenza outbreaks at World Youth Day 2008", J Clin Virol. (Dec. 1, 2009) 46(4):384-386.

Goldmeyer et al., "Identification of *Staphylococcus aureus* and Determination of Methicillin Resistance Directly from Positive Blood Cultures by Isothermal Amplification and a Disposable Detection Device", J Clin Microbiol. (Apr. 2008) 46(4): 1534-1536.

Gulliksen et al., "Towards a 'Sample-In, Answer-Out' Point-of-Care Platform for Nucleic Acid Extraction and Amplification Using an HPV 46/E7 mRNA Model System", J Oncol. (Epub: Dec. 2011) Article ID 905024; 12 pages, doi:10.1155/2012/905024.

Holland et al., "Biological sample collection and processing for molecular epidemiological studies", Mutation Res. (2003) 543:217-234.

Liao et al., "Comparison of viral isolation and multiplex real-time reverse transcription-PCR for confirmation of respiratory syncytial virus and influenza virus detection by antigen immunoassays", J Clin Microbiol. (Mar. 2009) 47(3):527-532. Epub Jan. 7, 2009.

Luo et al., Electrochemical techniques on sequence-specific PCR amplicon detection for point-of-care applications, Analyst (Oct. 2009) 134(10):1957-1964. Epub Aug. 18, 2009.

MagNA® Pure Compact RNA Isolation Kit I, Package Insert, Roche, Version Nov. 2005; pp. 24.

MagNA® Pure LC mRNA Isolation Kit I—Lysis Buffer—Refill; Package Insert; Roche, Version Jun. 2004; pp. 2.

Neuzil et al., "Rapid detection of viral RNA by a pocket-size real-time PCR system", Lab Chip (Oct. 7, 2010) 10(19):2632-2634. Epub Jul. 30, 2010.

Qiu et al., "A large volume, portable, real-time PCR reactor", Lab Chip (Nov. 21, 2010) 10(22):3170-3177. Epub Oct. 6, 2010.

RNeasy® Mini Handbook for Kit.—Third Edition; Qiagen. Jun. 2001; pp. 116.

Superscript III One-Step RT-PCR System with Platinum. Kit Handbook. Invitrogen Feb. 1, 2001; Rev. Sep. 23, 2003; pp. 4.

International Search Report and Written Opinion dated Jul. 17, 2013 for Application No. PCT/US2013/031072, filed Mar. 13, 2013.

BinaxNOW Influenza A and B Test Kit: Kit Product Instructions; 2005; 5 pages.

Jiang, J. et al., "A universal pre-analytic solution for concurrent stabilization of salivary proteins, RNA and DNA at ambient temperature", Ach Oral Biol., (Mar. 2009) 54(3): 268-273.

USAID, "Avian Influenza Commodities Training Guide", Mar. 2007; 24 pages.

\* cited by examiner

REFLEX TESTING OF SAMPLES USING RESIDUAL MATERIALS FROM A PRIOR TEST

CROSS REFERENCE TO RELATED APPLICATIONS

The present application is a continuation of International Application No. PCT/US2013/031072, filed Mar. 13, 2013, which claims priority to U.S. Provisional Application Ser. No. 61/624,198, entitled "REFLEX TESTING OF SAMPLES USING RESIDUAL MATERIALS FROM A PRIOR TEST," filed Apr. 13, 2012. Each of the above applications is hereby incorporated by reference in its entirety.

BACKGROUND

Technical Field

Embodiments disclosed herein relate to methods and systems for performing sequential, automated assays, such as nucleic acid testing assays.

Description of the Related Art

Automation of molecular testing of samples has become increasingly common, due in part because automation can reduce the amount of time from sample collection to receiving results, can minimize experimental variability and can reduce the need for highly trained technicians. In addition to benefits in the field of diagnostics, automation of processing and testing samples has facilitated high throughput testing. Automated devices for specimen and or sample processing typically include hardware and consumables. It is thus desirable to maximize automation of molecular testing, while minimize the amount of consumables used.

The embodiments described provide for improved automated specimen and/or sample testing that can advantageously be used in clinical and research settings.

SUMMARY

The present technology relates to methods and systems for performing sequential assays, such as nucleic acid testing assays. Some embodiments relate to sequential assays on one or more specimens performed on an automated instrument. In some embodiments of the technology presented herein, methods of performing an automated assay on a plurality of samples are provided that allow for improved reliability and ease of use assaying a plurality of specimens on an automated instrument. The methods can include a) providing an automated instrument configured to receive and process a plurality of samples from the plurality of specimens for one or more target analytes according to one or more respective assay workflows; b) providing a plurality of samples to be tested; c) automatically transferring a first portion of each of the plurality of samples to be tested to a respective plurality of first vessels that comprise reagents for a first test for a first target analyte; d) automatically performing the first test on the portion of the plurality of samples to determine the presence of a first target analyte according to a first assay workflow; e) selecting a subset samples from the plurality of samples in which the presence of the first target analyte was determined; f) automatically transferring a second portion of the selected subset of samples from e) to a second vessel comprising reagents for a second test to determine the presence of a second target analyte according to a second assay workflow; and g) automatically performing the second test on the second portion of the selected subset of samples.

In some embodiments, each of the plurality of samples comprises a pre-processed solution of isolated nucleic acids from a respective plurality of specimens. In some embodiments, the automated instrument automatically processes the plurality of specimens to obtain the respective plurality of samples comprising isolated nucleic acids.

In some embodiments, for each sample, the sample and the first vessel comprising reagents for a first test are located on a first test strip, and such that step f) further comprises automatically transferring the second portion of the sample to the second vessel comprising reagents for the second test located on a second test strip.

In some embodiments, step e) further comprises e1) identifying a subset of the plurality of first test strips for the second test; and e2) for each first test strip in the subset, providing a corresponding second test strip comprising a vessel comprising reagents for a second test for a second analyte.

In some embodiments, the second test strip comprises at least one pipette tip. In some embodiments, the method comprises, prior to step f), adding additional liquid to the sample.

In some embodiments, for each sample, the sample, the first vessel, and a receptacle for the second vessel are located on a single test strip. In some embodiments, method comprises, prior to step e), the steps of d1) identifying a subset of the plurality of first test strips for testing for the second analyte; and d2) for each test strip in the subset, providing the second vessel comprising reagents for the second test in the receptacle.

In some embodiments, the method comprises, prior to step f), the step of providing a pipette tip configured to transfer the second portion of the sample to the second vessel comprising reagents for the second test.

In some embodiments, the pipette tip can be, for example, an unused pipette tip or a washed pipette tip. In some embodiments, the method comprises, prior to step f), the step of adding additional liquid to the sample comprising.

In some embodiments, the first or the test comprises a reaction selected from the group selected from: Polymerase Chain Reaction (PCR), Transcription Mediated Amplification (TMA), Oligonucleotide Ligation Assay (OLA), Ligase Chain Reaction (LCR), Rolling Circle Amplification (RCA), Strand Displacement Amplification (SDA), and a hybridization reaction.

In some embodiments, the method further comprises the step of comparing identifying indicia on a test strip to a set of assay-specific identifying data stored on the instrument.

Also presented herein is a system for performing an automated assay on a plurality of samples from a respective plurality of specimen, the system comprising an automated instrument configured to receive and process a plurality of samples according to one or more assay workflows; the instrument comprising a plurality of test strips; a processor; a storage capacity; and a program for performing an automated assay, the program comprising instructions for a) providing an automated instrument configured to receive and process a plurality of samples according to one or more assay workflows, the instrument comprising a plurality of test strips; b) automatically transferring a first portion of each sample to a respective plurality of first vessels comprising reagents for a first test; c) performing the first test to determine the presence of a first target analyte; d) automatically transferring a second portion of the samples, or a selected subset of the samples, to respective second vessels comprising reagents for a second test; and e) performing a second test on the second portion of the samples, or selected subset of samples, to determine the presence of a second target analyte.

In some embodiments of the above system, the program further comprises instructions for automatically isolating nucleic acid from the plurality of specimens, to obtain a respective plurality of samples comprising isolated nucleic acids.

In some embodiments of the above system, for each sample, the samples and the first vessel comprising reagents for the first test are situated on a first test strip, and wherein step e) comprises automatically transferring a portion of the extracted nucleic acid solution to a second master mix tube situated on a second test strip.

In some embodiments of the above system, for each sample, the sample, the first vessel, and a receptacle for the second vessel are located on a single test strip, wherein the program comprises instructions for the steps of d1) identifying a subset of the plurality of first test strips for testing for the second analyte; and d2) for each test strip in the subset, providing a corresponding second vessel comprising reagents for the second test in the receptacle.

Also presented herein is a method of performing reflex testing on a plurality of specimens, the method comprising a) providing a plurality of specimens to be tested; b) processing the plurality of specimens to obtain a respective plurality of samples; c) transferring a first portion of each of the plurality of samples to be tested to a respective plurality of first vessels that comprise reagents for a first test for a first target analyte; d) performing the first test on the portion of the plurality of samples to determine the presence of a first target analyte; e) selecting a subset samples from the plurality of samples in which the presence of the first target analyte was determined for the reflex test; f) transferring a second portion of the selected subset of samples from e) to a second vessel comprising reagents for a second test to determine the presence of a second target analyte; and g) performing the second test on the second portion of the selected subset of samples.

In some embodiments of the above methods, the first test comprises a test for the simultaneous detection of methicillin resistant *Staphylococcus aureus* and *Staphylococcus aureus*, and wherein the second test comprises a test for the detection of a determinant for mupirocin resistance. In some embodiments, the determinant for mupirocin resistance comprises the mupA gene.

Also presented herein is a method of performing reflex testing on a specimen, the method comprising a) providing a specimen to be tested; b) processing the specimen to obtain a respective sample; c) transferring a first portion of the sample to be tested to a first vessel comprising reagents for a first test for a first target analyte; d) performing the first test on the first portion of the sample to determine the presence of the first target analyte; f) transferring a second portion of the sample to a second vessel comprising reagents for a second test to determine the presence of a second target analyte, if the first target analyte is detected in the first portion of the sample; and g) performing the second test on the second portion of the sample.

In some embodiments of the above method, the first test comprises a test for the simultaneous detection of methicillin resistant *Staphylococcus aureus* and *Staphylococcus aureus*, and wherein the second test comprises a test for the detection of a determinant for mupirocin resistance. In some embodiments, the determinant for mupirocin resistance comprises the mupA gene.

DETAILED DESCRIPTION

Figure 1:
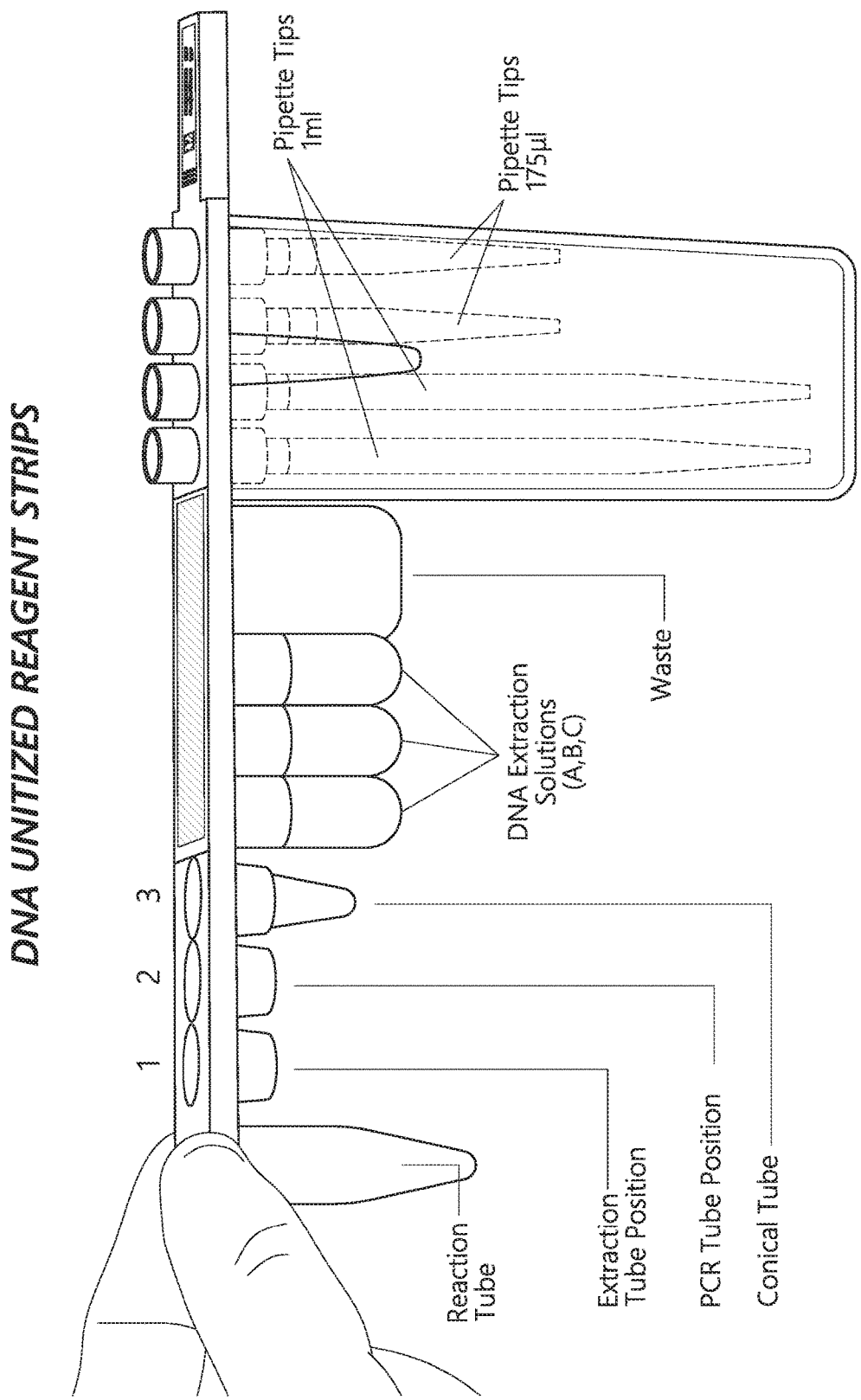
FIG. 1 shows a test strip according to one embodiment.

The section headings used herein are for organizational purposes only and are not to be construed as limiting the subject matter described in any way. All literature and similar materials cited in this application including, but not limited to, patents, patent applications, articles, books, treatises, and internet web pages, regardless of the format of such literature and similar materials, are expressly incorporated by reference in their entirety for any purpose. In the event that one or more of the incorporated literature and similar materials defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Automated diagnostic instruments capable of processing and testing multiple specimens and/or samples in parallel have been described. These devices can advantageously be used in high throughput to facilitate the specimen and/or sample preparation and testing. By way of example, automated diagnostic instruments can prepare samples for diagnostic assays such as nucleic acid amplification assays, and perform amplification and detection.

Diagnostic tests are, by nature, hypothesis-driven. When conducting a hypothesis driven test, such as testing a sample for a specific analyte, the result of the test can lead to a desire to test for another target, i.e., a reflex test. However, many times it is only useful to test a subset of the original samples, and would not be cost effective to test all of the samples. By way of example, in a clinical setting, it may be desirable to test a specimen for one or more pathogens. If the test reveals the presence of a particular pathogen, it may be desirable to perform further testing, e.g., to determine the presence of antibiotic resistance determinants. Obtaining an additional specimen for further testing, e.g., from a patient whose specimen tested positive for an analyte indicative of the presence of a particular pathogen, can be difficult and can delay further testing that is desirable. In addition to the potential difficulty in obtaining multiple specimens for testing, if multiple specimens are being tested, manual approaches to transfer patient specimens, or samples prepared from the specimens for testing (e.g., nucleic acid testing) to a new reaction vessel can be error prone, as well as inefficient and labor intensive. Further, when specimens need to be processed prior to testing, it is desirable to minimize the costs associated with processing (e.g., reagents, and the like). Thus, there exists a great need for improved methods to perform reflex testing, in an automated way.

Accordingly, a "reflex test" refers to a subsequent test (e.g., a second test) that is undertaken based upon the results obtained in a previous test (e.g., a first test). Non-limiting examples of first tests and reflex tests include, for example, a first test for methicillin-resistant *Staphylococcus aureus* MRSA and methicillin-sensitive *S. aureus* (MSSA). For samples that test positive for MRSA or MSSA, it may also be desirable to determine whether the samples contain determinants for mupirocin (an antibiotic) resistance. As mupirocin resistance is typically relevant only for MRSA or MSSA positive samples, it is often not cost effective to test samples negative for MRSA and MSSA for mupirocin resistance. Various tests and reflex tests useful in the embodiments disclosed herein are discussed in further detail below.

The methods and systems presented herein advantageously use residual material from the original test rather than require a new specimen to be obtained from the patient. For example, it can be especially advantageous to use residual material that has been highly processed and requires little additional effort to conduct the reflex test.

Specimens and Samples

The embodiments disclosed herein can be used to test specimens using automated molecular assays. As used herein, the term "specimen" can refer to a clinical specimen or sample from one or any number of sources, including, but not limited to, bodily fluids (including, but not limited to, blood, urine, serum, lymph, saliva, anal and vaginal secretions, perspiration, peritoneal fluid, pleural fluid, effusions, ascites, purulent secretions, lavage fluids, drained fluids, brush cytology specimens, biopsy tissue, explanted medical devices, infected catheters, pus, biofilms and semen) of virtually any organism, with mammalian samples, particularly human samples, and environmental samples (including, but not limited to, air, agricultural, water and soil samples) finding use in the invention. In addition, samples can be taken from food processing, which can include both input samples (e.g. grains, milk or animal carcasses), samples in intermediate steps of processing, as well as finished food ready for the consumer.

In some embodiments, samples are prepared from specimens, and tests are performed on the samples. For example, in some embodiments, specimens can be processed in order to obtain samples suitable for molecular testing. In some embodiments, specimens can be analyzed directly, and are not pre-processed prior to testing. For example, a "direct sample" is a specimen that is collected from a subject and tested using the methods disclosed herein without isolating or culturing bacteria from the specimen, or without processing the specimen to isolate nucleic acids prior to testing. As such, direct samples are generally only minimally processed prior to screening. In some embodiments, the specimens disclosed herein are processed to obtain samples suitable for testing. For example, specimens containing cells can be processed to lyse cells and release the cellular components such as nucleic acids, proteins, and the like, prior to testing. In some embodiments, specimens can be processed to produce samples that include isolated nucleic acids. As used herein, the phrase "isolate nucleic acids" refers to the purification of nucleic acids from one or more cellular components. The skilled artisan will appreciate that samples processed to "isolate nucleic acids" therefrom can include components and impurities other than nucleic acids. Samples that comprise isolated nucleic acids can be prepared from specimens using any acceptable method known in the art. For example, cells can be lysed using known lysis agents, and nucleic acids can be purified or partially purified from other cellular components. Suitable reagents, and protocols for DNA and RNA extractions can be found in, respectively, U.S. Patent Application Publication Nos. US 2010-0009351, and US 2009-0131650, each of which is incorporated herein by reference in its entirety. In nucleic acid testing (e.g., amplification and hybridization methods discussed in further detail below), the extracted nucleic acid solution can be added directly to a reagents (e.g., either in liquid, bound to a substrate, in lyophilized form, or the like, as discussed in further detail below), required to perform a test according to the embodiments disclosed herein.

In some embodiments, the tests, e.g., the first tests and the reflex tests, described herein are tests to determine the presence of a target analyte in a specimen or sample. As used herein, the term "target analyte" can refer to various types of analytes of interest, including for example, target nucleic acids, target proteins, or other target molecules of interest. In some embodiments, the devices and methods described herein are used to perform reflex tests to determine the presence of target nucleic acids, although the skilled artisan will appreciate that the embodiments disclosed herein can be readily adapted to test for other types of target analytes.

In accordance with the above, the embodiments provided herein advantageously provide improved methods of automatically testing specimens and samples for target analytes. The methods for performing an automated assay on a plurality of samples. In some embodiments, the method can a) providing an automated instrument configured to receive and process a plurality of samples from said plurality of specimens for one or more target analytes according to one or more respective assay workflows; b) providing a plurality of samples to be tested; c) automatically transferring a first portion of each of said plurality of samples to be tested to a respective plurality of first vessels that comprise reagents for a first test for a first target analyte; d) automatically performing the first test on the portion of said plurality of samples to determine the presence of a first target analyte according to a first assay workflow; e) selecting a subset samples from the plurality of samples in which the presence of the first target analyte was determined; 0 automatically transferring a second portion of the selected subset of samples from e) to a second vessel comprising reagents for a second test to determine the presence of a second target analyte according to a second assay workflow; and g) automatically performing the second test on the second portion of the selected subset of samples.

Automated instruments useful in the embodiments disclosed herein can include, for example, those described in U.S. Pat. No. 8,133,671, U.S. Patent Application Publication No. 2009-0111059, herein incorporated by reference in their entireties. The skilled artisan will appreciate that the embodiments disclosed herein can be readily adaptable to any suitable automated system for specimen and/or sample processing and testing, however. Desirably, the automated systems are configured to enable processing or testing of a plurality of samples according to one or more workflows. As used herein, the terms "workflow," "assay workflow," "assay," "assay protocol," "test," and like terms refer to a procedure for processing a specimen and/or sample. In typical embodiments, a workflow can include sample preparation steps, such as cell lysis, nucleic acid extraction, nucleic acid purification, nucleic acid digestion, nucleic acid modification, protein extraction, protein purification, and the like. Several methods of nucleic acid extraction useful in the embodiments disclosed herein are known in the art. Exemplary discussions of nucleic acid extraction can be found, for example, in U.S. Patent Application Publication No. 2009-0131650, U.S. Patent Application Publication No. 2010-0009351, and U.S. Patent Application Publication No. 2006-016623311/281,247, herein incorporated by reference in their entireties. Likewise, exemplary discussions of protein extraction can be found, for example, in U.S. Pat. Nos. 8,053,239 and 6,864,100, herein incorporated by reference in their entireties.

In some typical embodiments, a workflow can also include nucleic acid amplification reactions. In some typical embodiments, a workflow can further include data analysis procedures.

As described above, in some embodiments, a portion (e.g., a first portion, and, in some cases, a second portion) of the sample being assayed or analyzed is transferred to a vessel that contains reagents for a test. As used herein, the term "vessel" refers to any type of object capable of holding a sample, including but not limited to, tubes, vessels in microtiter plates, and the like. In some embodiments, the vessel is located within a test strip. As used herein, the term "test strip" or "reagent strip" refers to a package that holds one or more consumable components for an automated assay. The test strips can therefore be configured for use by an apparatus that carries out automated specimen and/or sample preparation, such an apparatus is described, e.g., in International Patent Application Publication. No. WO 09/054,870, incorporated herein by reference in its entirety.

Figure 2:
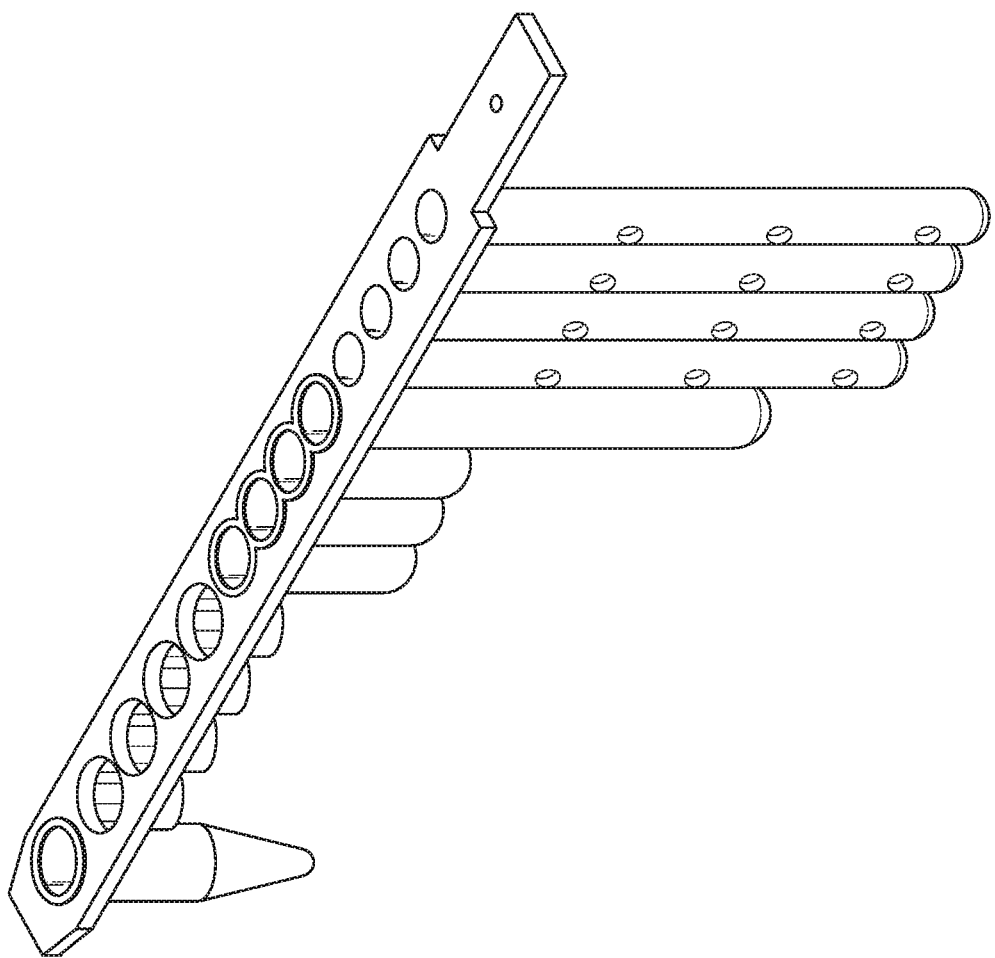
FIG. 2 shows a test strip according to one embodiment.

In typical embodiments, a test strip can comprise a vessel, such as a tube, well or the like, for holding a pre-processed sample, solution comprising isolated nucleic acids obtained from a specimen. Typically, the test strip can also comprise a vessel for holding reagents for a molecular test, such as a nucleic acid test (e.g., reagents used in nucleic acid amplification, as discussed in further detail elsewhere herein). In some embodiments, the test strip can include additional vessels for conducting sample preparation and for holding reagents and other consumables, such as pipette tips. In some embodiments, the test strip or reagent strip includes one or more receptacles or apertures that are configured to receive reaction vessels that contain assay reagents. Accordingly, in some embodiments, vessels that contain reagents for use in the assays described herein are unitary or integral with the test strip, whereas in some embodiments, vessels that contain reagents for use in the assays described herein are not integral with the test strip, but are adapted to snap into a receptacle or aperture in the test strip. Non-limiting examples of test strips or reagent strips useful in the embodiments disclosed herein are set forth in FIGS. 1 and 2, in U.S. Pat. Nos. D618820, D637737, and in U.S. Provisional Patent Application No. 61/541,991 filed Sep. 30, 2011 and entitled "UNITZED REAGENT STRIP", each of which is hereby incorporated by reference in its entirety. FIG. 1 and FIG. 2 illustrate exemplary test strips/reagent strips useful in the embodiments disclosed herein.

An automated instrument may comprise or be configured to receive, e.g., in a dock, one or more strip carriers, each strip carrier or racks capable of holding a plurality of test strips, and optionally tubes, e.g., tubes for carrying specimens. In typical embodiments, the test strips are positioned in one or more strip carriers or racks that are accommodated by the automated instrument. Exemplary strip carriers or racks useful in the embodiments disclosed herein are disclosed in, e.g., U.S. Patent Application Publication No. 2009-0136386, although the skilled artisan will appreciate that various other configurations of strip holders or racks suitable for use with an automated system as described herein can be used. In some embodiments, the test strip carriers or racks are configured to hold a plurality of test strips or reagents strips, e.g., in various lanes. For example, the test strip carrier can contain 2, 3, 4, 5, 6, 7, 8, 9, 10, 11, 12, 13, 14, 15, 16, 17, 18, 19, 20, 21, 22, 23, 24, or more, lanes, configured to accommodate anywhere from 2-24 respective test strips or reagent strips.

In the methods disclosed herein, depending upon the results of the first test performed on the sample, a reflex test is performed. If results from the first test reveal the desirability of performing the reflex (subsequent) test, according to the methods disclosed herein, a second (or residual) portion of the sample left over following the first test procedure, is automatically transferred a to a second vessel that comprises reagents for the reflex (subsequent test). The automatic transfer of the second portion of the sample can be performed in any one of a number of methodologies. For example, in some embodiments, the vessel containing the remainder or residual portion of the sample following the first test, can be transferred to a second test strip, after which, at least a portion of the sample is then automatically transferred to a vessel containing reagents for a second test. In some embodiments, the second portion of the sample is automatically transferred directly from the first test strip to a second master mix tube positioned in a second test strip. In some embodiments, the second portion of the sample can be automatically transferred directly from the first test strip to a second vessel positioned the first test strip. It will be appreciated that although several embodiments are described in greater detail below, any suitable methodology of automatically transferring the extracted nucleic acid solution to a second master mix tube can be performed according to the methods provided herein.

Transfer to a New Test Strip

In certain embodiments, for each sample, the sample and a vessel or tube comprising reagents for the first test are situated on a single test strip, e.g., a first test strip, and the step of automatically transferring a portion of the sample involves automatically transferring a second portion of the sample to a second master mix tube situated on a second, discrete, test strip.

Figure 3:
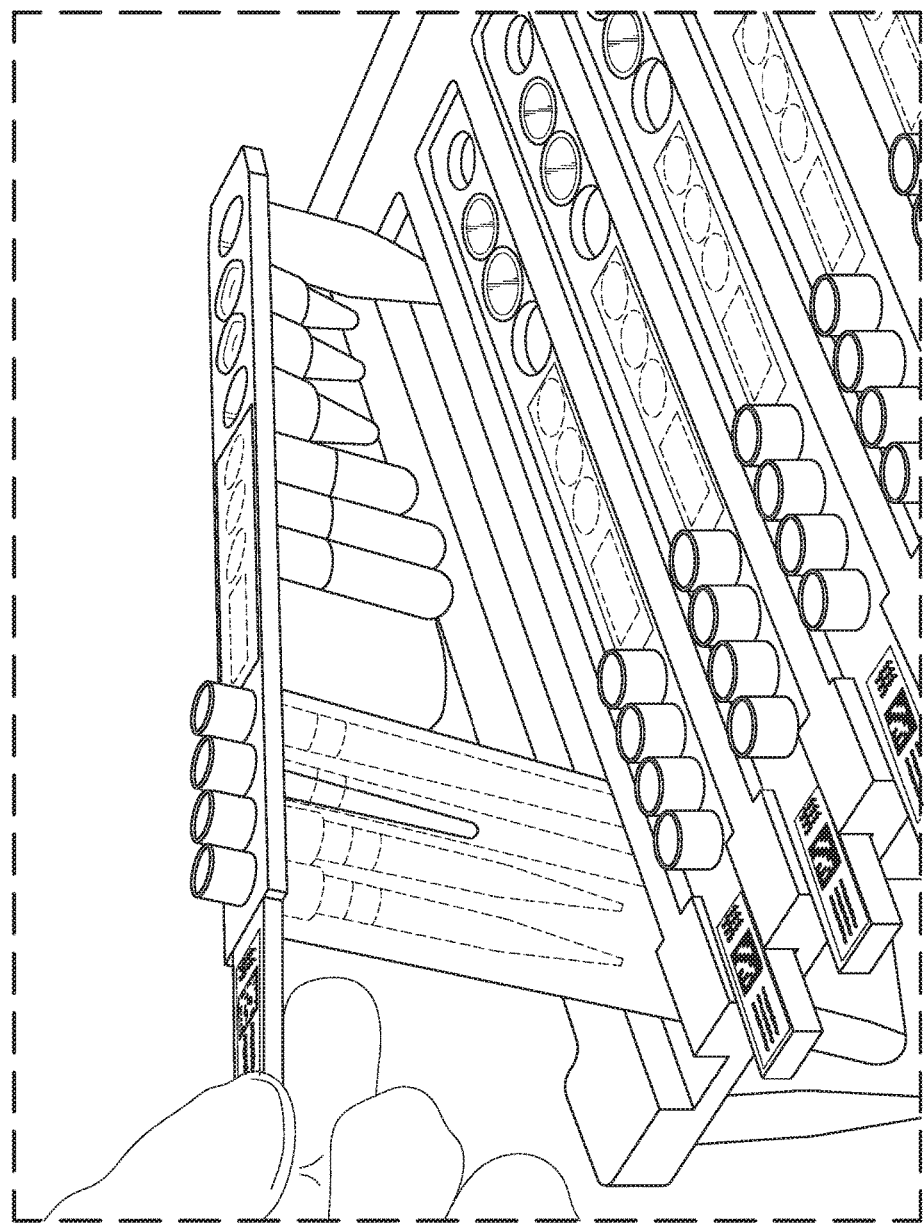
FIG. 3 shows multiple test strips placed in a strip carrier according to one embodiment.

In some embodiments, the first and second test strips are situated in separate strip carriers, or racks. As one non-limiting example, the first test strips can be positioned in lanes 1-6 of a first strip carrier, and the second test strips can be positioned in lanes 1-6 of a second strip carrier. An example of test strips positioned in a strip carrier is shown in FIG. 3.

In some embodiments, the first and second test strips are situated in the same strip carrier. As one non-limiting example, the first test strips are positioned in lanes 1, 3, 5, 7, 9 and 11 and corresponding second test strips can be placed into lanes 2, 4, 6, 8, 10 and 12 of the same strip carrier. As another non-limiting example, the first test strips can be positioned in lanes 1-6 and the corresponding second test strips can be positioned in lanes 7-12 of the same strip carrier. It will be appreciated that any suitable configuration of positioning for first and second test strips can be used. In some embodiments, the automated instrument can use identifying indicia such as a barcode, RFID code, or the like, on each test strip to identify the position of the first and/or second test strip. In some embodiments, the method further comprises the step of comparing identifying indicia on a test, strip, a vessel within a test strip, or a specimen tube, to a set of assay-specific identifying data stored on the instrument.

Thus, in some embodiments, the user can select one or more first test strips for a second, reflex test and transfer the one or more selected test strips into a new rack that contains second test strips, having vessels comprising reagents for the second, reflex test. In some embodiments, the user can select one or more of the first test strips for a second, reflex test, and the automated instrument or user can transfer a second portion of the sample to a second test strip located in a second, discrete test strip carrier or rack. In some embodiments, identifying indicia on specimen tubes, or test strips used in the first test can be accessed the automated instrument, and this information can be used to track samples as they are processed during a second, or reflex test. Accordingly, in some embodiments of the above-described methods, the method can comprise, prior to transferring a second portion of the sample to a second vessel, identifying a subset of the plurality of first test strips for further testing, e.g., for a second test; and for each first test strip in the subset, providing a corresponding second test strip. The second test strip can include the second vessel containing reagents for the second test. In certain embodiments, the second test strip can also include at least one pipette tip.

Transfer to the Same Test Strip

In certain embodiments, for each sample, the sample solution and the first vessel that includes reagents for the first test are situated on a first test strip, and the step of transferring a portion of the extracted nucleic acid solution comprises transferring a portion of the extracted nucleic acid solution to a second vessel containing reagents for a second test that is also located on the first test strip.

In some embodiments of the above-described methods, the method can include, prior to transferring a second portion of the sample to a second vessel, the steps of identifying a subset of the plurality of samples for further testing, e.g., for a second or reflex test; and for each of the samples identified for further testing, providing a corresponding second vessel including reagents for the second or reflex test on the first test strip. In a typical embodiment, the first test strips are configured with an open position, e.g., a receptacle or vessel, suitable for adding an additional master mix tube to the strip. For example, the test strip can be a 4-snap strip, as illustrated in FIG. 2, which allows the user to add the reflex master mix to the open position. In some embodiments, the test strips are arranged by the user in a new test strip holder or rack prior to performing the second or reflect test.

The skilled artisan will appreciate that it is desirable to minimize the risk of cross-contamination of reagents from the first test and reagents from the second, or reflex, test. Accordingly, in some embodiments, the consumables such as pipette tips can be replaced and/or cleaned using residual buffers in the test strip prior to conducting the reflex test. Thus, in certain embodiments, the method comprises, prior to transferring the second portion of the sample to the second vessel, the step of providing a pipette tip. In some embodiments, the pipette tip is an unused pipette tip. In some embodiments, the pipette tip is a used tip that has been washed to reduce or avoid contamination from previous liquid transfers. In certain embodiments, the method comprises, prior to transferring the second portion of the sample to the second vessel, the step of washing a pipette tip that was used during the first test.

During the processing and/or testing of the samples prior to a second, reflex test, evaporation of the sample may occur. As such, sample evaporation can reduce performance of a reflex test. The embodiments disclosed herein provide a solution to evaporation, by using a fixed volume buffer, e.g., a wash buffer or nucleic acid elution buffer, to add to the residual sample to ensure that there is sufficient volume to further process the residual sample, e.g., in a second, or reflex test. Accordingly, in some embodiments, the method comprises, prior to performing a second or reflex test, the step of adding additional liquid to the residual sample. By way of example only, in some embodiments, the initial volume of a sample can range from 1 µL-1 ml, and preferably is between 10 µL and 200 µL, e.g., 25-75 µL. In some embodiments, a first portion of about 5-25 µL, e.g, 10-20 µL of the sample, is removed for the first test. By way of example, in some embodiments, 12.5 µL of the initial sample is used in the first test. In order to ensure that a sufficient volume of sample is available for the second test, in some embodiments, an additional volume of 0.5 µL, 1 µL, 2 µL, 3 µL, 4 µL, 5 µL, 6 µL, 7 µL, 8 µL, 9 µL, 10 µL, 12 µL, 14 µL, 16 µL, 18 µL, 20 µL, 25 µL, 30 µL, 35 µL, 40 µL, 45 µL, 50 µL, 55 µL, 60 µL, 65 µL, 70 µL, 75 µL, 80 µL, 85 µL, 90 µL, 95 µL, 100 µL, 120 µL, 140 µL, 160 µL, 180 µL, 200 µL, 300 µL, 400 µL, 500 µL, or more than 500 µL of additional liquid may be added to increase the liquid volume prior to transfer of a second portion of the sample to a vessel containing reagents for a second, or reflex test. Accordingly, the addition of solution to the remaining or residual sample can compensate for evaporation that may occur before the solution is transferred to the second master mix. In some embodiments, a volume equal to 0.1%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 120%, 140%, 160%, 180%, 200%, 250%, 300%, 350%, 400% or more, relative to the volume of extracted nucleic acid solution remaining after the first aliquot is transferred to the first master mix, may be added to increase the liquid volume and compensate for evaporation that may occur before the solution is transferred to the vessel with reagents for a second test.

Nucleic Acid Testing (NAT) Assays and Reagents for NAT

As discussed above, the tests described herein can include, for example nucleic acid testing. In some embodiments, the tests include testing for target nucleic acid sequences in a sample. Several forms of nucleic acid testing are useful in the embodiments disclosed herein, including but not limited to, testing that involves nucleic acid amplification reactions. Several nucleic acid amplification reactions are known, and can be used to determine the presence of target nucleic acids in accordance with the embodiments disclosed herein. Methods of nucleic acid amplification can include, but are not limited to: polymerase chain reaction (PCR), strand displacement amplification (SDA), for example multiple displacement amplification (MDA), loop-mediated isothermal amplification (LAMP), ligase chain reaction (LCR), immuno-amplification, and a variety of transcription-based amplification procedures, including transcription-mediated amplification (TMA), nucleic acid sequence based amplification (NASBA), self-sustained sequence replication (3SR), and rolling circle amplification. See, e.g., Mullis, "Process for Amplifying, Detecting, and/or Cloning Nucleic Acid Sequences," U.S. Pat. No. 4,683,195; Walker, "Strand Displacement Amplification," U.S. Pat. No. 5,455,166; Dean et al, "Multiple displacement amplification," U.S. Pat. No. 6,977,148; Notomi et al., "Process for Synthesizing Nucleic Acid," U.S. Pat. No. 6,410,278; Landegren et al. U.S. Pat. No. 4,988,617 "Method of detecting a nucleotide change in nucleic acids"; Birkenmeyer, "Amplification of Target Nucleic Acids Using Gap Filling Ligase Chain Reaction," U.S. Pat. No. 5,427,930; Cashman, "Blocked-Polymerase Polynucleotide Immunoassay Method and Kit," U.S. Pat. No. 5,849,478; Kacian et al., "Nucleic Acid Sequence Amplification Methods," U.S. Pat. No. 5,399,491; Malek et al., "Enhanced Nucleic Acid Amplification Process," U.S. Pat. No. 5,130,238; Lizardi et al., BioTechnology, 6:1197 (1988); Lizardi et al., U.S. Pat. No. 5,854,033 "Rolling circle replication reporter systems." In some embodiments, two or more of the listed nucleic acid amplification methods are performed, for example sequentially.

As discussed above, in some embodiments, portions of a sample are transferred to a vessel containing reagents for a test. For example, in some embodiments, the samples are transferred to a vessel that contains a "master mix" for a test or reaction, such as an amplification reaction or the like. The "master mix" can include some, or all of the components necessary for a reaction, including, but not limited to enzymes, oligonucleotides, probes, salts, deoxynucleotide triphosphates, which comprises a polymerase enzyme and a plurality of nucleotides. In some embodiments, the master mix can further comprise hybridization probes with detectable moieties, wherein the probes specifically hybridize to target nucleic acids (and/or positive control target nucleic acid sequences). In some embodiments, a master mix can be provided at a higher concentration than will be used in a reaction. In some embodiments, a master mix is provided in a lyophilized form, and reconstituted at a higher concentration that will be used in the reaction. In some embodiments a master mix includes reagents at a concentration of at least about 2× of the reaction concentration, for example 2×, 2.5×, 3×, 4×, 5×, 6×, 7×, 8×, 9×, 10×, 15×, 20×, 25×, 40×, 50×, 100×, 200×, 250×, or 500×.

In some embodiments, the master mix can be in the form of one or more lyophilized pellets, as stored in a reagent tube on the test strip, and the method can further include reconstituting the reagent pellet with liquid, e.g., a portion of a sample as described herein above to create a reaction/reagent mixture solution that is suitable for processing, e.g. testing.

In some embodiments, a "master mix" or can be provided in a vessel includes identifying indicia, such as a bar code, RFID code, or the like, that provides identifying information regarding the reagents contained therein, e.g., indicia that identify that the vessel contains reagents for the detection of a particular target analyte.

Instruments and Systems

Also presented herein is a system for performing an automated assay, the system comprising an automated instrument configured to receive and process a plurality of specimens or samples according to one or more assay workflows described herein above.

The system can also include a processor; a storage capacity; and a program for performing an automated assay. For example, the program can include instructions for an automated instrument configured to receive and process a plurality of samples according to one or more assay workflows as described herein. The program can include instructions for receiving and processing a plurality of samples according to one or more workflows, wherein the samples are provided on a plurality of test strips; automatically transferring a first portion of each sample to a respective plurality of first vessels comprising reagents for a first test; performing the first test to determine the presence of a first target analyte; automatically transferring a second portion of the samples, or a selected subset of the samples, to respective second vessels comprising reagents for a second test; and performing a second test on the second portion of the samples, or selected subset of samples, to determine the presence of a second target analyte.

Automated instruments which can perform multiple assay protocols concurrently are known to those of skill in the art, and include but are not limited to, BD MAX® (Becton Dickinson and Co., Franklin Lakes, N.J.), the VIPER® (Becton Dickinson and Co., Franklin Lakes, N.J.), the VIPER LT® (Becton Dickinson and Co., Franklin Lakes, N.J.), the SMARTCYCLER® (Cepheid, Sunnyvale, Calif.), ABI PRISM 7700® (Applied Biosystems, Foster City, Calif.), ROTOR-GENE™ (Corbett Research, Sydney, Australia), LIGHTCYCLER® (Roche Diagnostics Corp, Indianapolis, Ind.), ICYCLER® (BioRad Laboratories, Hercules, Calif.), IMX4000® (Stratagene, La Jolla, Calif.), CFX96™ Real-Time PCR System (Bio-Rad Laboratories Inc), and the like. Exemplary discussions of typical automated instruments for use with the methods provided herein can be found, for example, in U.S. Pat. No. 8,133,671, which is incorporated herein by reference in its entirety.

It will be appreciated that the methods and systems described herein can apply to instruments that comprise 2, 3, 4 or more workstations wherein at least 2 of the workstations are supported by a common service resource. For example, an instrument with 4 workstations and a single pipette head could still be compatibility controlled by the 2 index concept described herein.

As used herein, the terms storage capacity, storage device, storage and the like can refer to any medium, device or means of storage of information. Storage can include, but is not limited to, a disk drive device such as a hard drive, floppy disk, optical or magneto-optical disk, memory such as RAM or ROM chips, and any other medium used to record or store data. In some embodiments, a storage capacity is connected to a processor which sends information to be recorded on the storage capacity after it is acquired. In specific embodiments, data is acquired by a system and is recorded on a storage capacity. In other embodiments, data is acquired by a system and information is first processed and the processed information is recorded on a storage capacity.

The files and programs provided herein can be in any suitable programming language. In certain embodiments, the ADF utilizes XML as a mechanism for formatting files. Further, in certain embodiments, ADF utilizes Python as a scripting language to provide a mechanism for executing result logic using common technologies available on the instrument. It will be appreciated that any suitable file format and programming language can be utilized in the methods and systems provided herein. In certain embodiments, files can be encrypted to protect against the use of counterfeit reagents and to control specific parameter details on assay runs.

As used herein, an "input" can be, for example, data received from a keyboard, rollerball, mouse, voice recognition system or other device capable of transmitting information from a user to a computer. The input device can also be a touch screen associated with the display, in which case the user responds to prompts on the display by touching the screen. The user may enter textual information through the input device such as the keyboard or the touch-screen.

The embodiments disclosed herein are operational with numerous other general purpose or special purpose computing system environments or configurations. Examples of well-known computing systems, environments, and/or configurations that may be suitable for use with the invention include, but are not limited to, microcontrollers, personal computers, server computers, hand-held or laptop devices, multiprocessor systems, microprocessor-based systems, programmable consumer electronics, network PCs, minicomputers, mainframe computers, distributed computing environments that include any of the above systems or devices.

As used herein, "instructions" refer to computer-implemented steps for processing information in the system. Instructions can be implemented in software, firmware or hardware and include any type of programmed step undertaken by components of the system.

A "microprocessor" or "processor" may be any conventional general purpose single- or multi-core microprocessor such as a Pentium® processor, Intel® Core™, a 8051 processor, a MIPS® processor, or an ALPHA® processor. In addition, the microprocessor may be any conventional special purpose microprocessor such as a digital signal processor or a graphics processor. A "processor" may also refer to, but is not limited to, microcontrollers, field programmable gate arrays (FPGAs), application-specific integrated circuits (ASICs), complex programmable logic devices (CPLDs), programmable logic arrays (PLAs), microprocessors, or other similar processing devices.

The system is comprised of various modules as discussed in detail herein. As can be appreciated by one of ordinary skill in the art, each of the modules comprises various sub-routines, procedures, definitional statements and macros. Each of the modules are typically separately compiled and linked into a single executable program. Therefore, the following description of each of the modules is used for convenience to describe the functionality of the preferred system. Thus, the processes that are undergone by each of the modules may be arbitrarily redistributed to one of the other modules, combined together in a single module, or made available in, for example, a shareable dynamic link library.

Certain embodiments of the system may be used in connection with various operating systems such as SNOW LEOPARD®, iOS®, LINUX, UNIX or MICROSOFT WINDOWS®.

Certain embodiments of the system may be written in any conventional programming language such as assembly, C, C++, BASIC, Pascal, or Java, and run under a conventional operating system.

In addition, the modules or instructions may be stored onto one or more programmable storage devices, such as FLASH drives, CD-ROMs, hard disks, and DVDs. One embodiment includes a programmable storage device having instructions stored thereon.

In some embodiments of the above system, the system further can comprise a device for reading identifying indicia on reagent packaging, e.g., on test strips, vessels containing reagents, as well as identifying indicial present on vessels that contain samples or specimens. It will be appreciated that any suitable device for reading identifying indicia can be used in the systems provided herein. Likewise, any suitable identifying indicia may be used that is compatible with the device on the instrument. Examples include bar codes, QR codes, RFID tags, color codes and the like. In typical embodiments, the device can be a bar code reader, and the identifying indicia can comprise a bar code.

Exemplary Reflex Assays

By way of another example, after a positive MRSA assay, a reflex assay for vancomycin resistance determinant(s), Panton-Valentine leukocidin (PVL) determinants, or to classify MRSA by spa-typing, or testing staphylococcal cassette chromosome mec (SCCmec) typing, can be performed for specimen that test positive for MRSA. Suitable tests for vancomycin resistance determinant(s), Panton-Valentine leukocidin (PVL) determinants, or to classify MRSA by spa-typing, or testing SCCmec are known in the art, as exemplified by Mak et al, J. Clin. Microbiol. (2009) 12:4136; Reischl et al. Eur. J. Clin. Microbiol. Infect. Dis. (2007) 26:131-135; Narukawa et al., Tohoku J. Exp. Med. (2009) 218:207-213; Chongtrakool et al., Antimicrob. Agents Chemother. (2006) 50:1001-1012; each of which is incorporated by reference in its entirety.

By way of another example, using a stool specimen from patients with severe diarrhea, first tested for *Clostridium difficile*, a reflex assay could be performed on positives to determine toxin subtype, or on negatives to test for a different causative organism. The converse is also true where stool specimens that are tested for an enteric panel could be reflexed to a *Clostridium difficile* test. Suitable tests for *Clostridium difficile*, and for toxin subtypes are known in the art, as exemplified by Kvach et al. J. Clin. Microbiol. (2010) 48:109-114; and Northey et al., J. Med. Microbio. (2005) 54:543-547; each of which is incorporated by reference in its entirety.

By way of another example, using a cerebro-spinal fluid specimen from patients with high fever, the specimens or samples can be first tested for a viral infection using a total nucleic acid test, and a second test can be performed on negatives to look for bacterial targets. Suitable tests for viral and bacterial infections are known in the art, as exemplified by Mahoney et al, J. Clin. Microbiol. (2007) 45:2965-2970 and Melendez et al. Clin. Microbiol. Infect. (2010) 16:1762-1769; each of which is incorporated by reference in its entirety.

By way of another example, using sputum specimens, the specimens or samples could be first tested for *Mycobacterium tuberculosis* complex (MTBC) and rifampin resistance. If there are positives, a reflex could be performed for Isoniazid and fluoroquinolone resistance in order to determine if the strain is MDR or XDR. Suitable tests for Mtbc, rifampin, isoniazid and fluoroquinolone resistance are known in the art, as exemplified by Somoskovi et al. J. Clin. Microbiol. (2003) 41:2822-2826; Saribas et al., J. Clin. Microbiol. (2003) 41:816-818; Rindi et al. J. Microbiol. Methods (2003) 55:797-800; Ip et al., J. Clin. Microbiol. (2006) 4:970-975; each of which is incorporated by reference in its entirety.

By way of another example, using bronchoalveloar aspirates in ICU patients, an initial screening for KPC/OXA/NDM carbapenemases can be performed. If negatives are found, a VIM/IMP screening could be performed. Suitable tests KPC/OXA/NDM detection and for VIM/IMP screening are known in the art, as exemplified by Nordmann et al. Clin. Microbiol. Infect. (2002) 8:321-331; and Monteiro et al. J. Antimicrob. Chemother. (2012); each of which is incorporated by reference in its entirety.

By way of another example, using a sample, and following a Gram stain or a maldi identification, an assay could be performed on a panel of resistance markers panel for Gram positive (if the Gram is positive) or a Gram negative panel (if the Gram is negative). Here the reflex strategy described is after another system or test for identification. Suitable tests for Gram positive and Gram negative screening are known in the art, as exemplified by Carroll et al. J. Clin. Microbiol. (2000) 5:1753-1757; which is incorporated by reference in its entirety.

By way of another example, using food samples or environmental samples, a *Listeria* spp. screening can be first performed. If positives are identified, a specific reflex assay for *L. monocytogenes* can be performed. Suitable tests detecting *Listeria* spp and *L. monocytogenes* are known in the art, as exemplified by Bubert A. App. Environ. Microbiol. (1999) 10:4688-4692; and Borucki et al., J. Clin. Microbiol. (2003) 41:5537-5540; each of which is incorporated by reference in its entirety.

By way of another example, using water samples or pharmaceutical environment samples, a TVC assay can be performed. If the initial assay is positive, a reflex assay can be performed for Gram positive or Gram negative or a specific assay towards *E. coli* or enterococci or *bacillus*. Suitable tests for TVC and for Gram positive and Gram negative screening are known in the art, as exemplified by Ereveeval et al., J. Clin. Microbiol. (2003) 41:5466-5472;

and Carroll et al. J. Clin. Microbiol. (2000) 5:1753-1757; each of which is incorporated by reference in its entirety.

Another exemplary embodiment relates to the testing of specimens from subjects having, or suspected of having cystic fibrosis. For example, a first test can be performed on samples or specimens from a subject to test for the presence of target analytes, e.g., target nucleic acid sequences, associated with *Psuedomonas aeruginosa*, and/or *Burkholderia cepacia*. Non-limiting examples of assays for the detection of *P. aeruginosa* and/or *B. cepacia* useful in the embodiments disclosed herein include, e.g., those described in Spilker et al. (2004), J. Clin. Microbiol. 42(5):2074-2079, and Vonberg et al., (2006), J. Med. Micriobiol. 55(Pt. 6):721-727. For samples testing positive for either pathogen, reflex tests for antibiotic resistance determinants can be performed, e.g., tests to determine target nucleic acids indicative of tetracycline, nalidixic acid, norfloacin, chloramphenicol, cirpfloxacin, or the like.

It will be appreciated that the above list is meant only to provide examples of the methods and systems provided herein, and that any suitable reflex assay could be performed based upon the outcome of an initial assay.

EXAMPLES

Having generally described this invention, a further understanding can be obtained by reference to certain specific examples which are provided herein for purposes of illustration only, and are not intended to be limiting.

Example 1

Identification of Samples for Reflex Analysis

This example describes the identification of samples for reflex analysis at the end of a PCR run using an automated instrument for sample preparation, processing and analysis. A panel of 12 biological specimens, each in an individual sample tube, is processed to obtain respective samples of solution comprising isolated nucleic acids. Each test strip includes a tube for cell lysis, indicated as "Reaction Tube" in FIG. 1. The test strip also includes positions for three additional tubes, indicated as positions 1, 2 and 3 in FIG. 1. At position 3 is a conical tube configured for holding the final extracted nucleic acid solution, or sample solution that includes isolated nucleic acids. As shown in FIG. 1, the test strip also comprises additional reservoir positions in the test strip to hold extraction solutions, a waste chamber to hold waste liquid, and several sheaths to hold disposable pipettes. The test strip is also configured with identifying indicia such as a bar code at one end of the strip.

The user places an extraction tube in position 1 and a master mix for detection and/or identification of methicillin-resistant *Staphylococcus aureus* (MRSA) and *S. aureus* (including methicillin sensitive *S. aureus*), e.g., the BD GENEOHMT™ StaphSR™ assay reagents (Becton Dickinson, Franklin Lakes, N.J.), in position 2 of each of the 12 test strips. Each specimen is automatically processed with lysis buffer in the reaction tube, and a portion of the resulting liquid is automatically transferred to the extraction tube, where bead-based nucleic acid extraction is performed using the extraction solutions and the final extracted nucleic acid solution sample is transferred to the conical tube at position 3. The total volume of the extracted nucleic acid solution sample in the conical tube of each test strip is 25 µL. An aliquot of 12.5 µL of the extracted nucleic acid solution is automatically pipetted to the adjacent master mix tube to reconstitute the StaphSR™ master mix. The master mix is transferred to a reaction cartridge for PCR analysis. After PCR, 6 of the 12 samples are indicated as positive for MRSA or *S. aureus*, and identified as candidates for mupirocin resistance, and are therefore selected for further analysis as set forth in the examples below.

Example 2

Manual Transfer of Extracted Nucleic Acid Solution to New Test Strip and Automatic Transfer to New Master Mix Tube for Reflex PCR Analysis Sample preparation and processing using PCR analysis for MRSA and *S. aureus* are performed as described above in Example 1. Each of the 6 used test strips corresponding to the samples identified for reflex analysis for mupirocin resistance are repositioned in lanes 1-6 of a new rack. New test strips are positioned in lanes 1-6 of a separate rack. An additional 15 µL of elution buffer is added to the remaining extracted nucleic acid solution in each test strip associated with positive samples from the StaphSR™ test performed in Example 1, above. A portion of the residual or remaining sample comprising isolated nucleic acids obtained from the specimen is transferred to position 3 of a new test strip. The user places a master mix for mupirocin resistance PCR analysis in position 2 of each of the 6 new test strips. An aliquot of 12.5 µL of the extracted nucleic acid solution is automatically pipetted to the adjacent master mix tube to reconstitute the master mix for the mupirocin resistance PCR analysis, using a new pipette situated on the new test strip.

The reflex PCR analysis indicates that a subset of the samples selected for the reflex test are positive for mupirocin resistance.

Example 3

Automatic Transfer of Extracted Nucleic Acid Solution to New Master Mix Tube on New Test Strip for Reflex PCR Analysis Sample processing and testing using the StaphSR™ assay are performed as described above in Example 1. Each of the 6 used test strips corresponding to the samples identified for reflex analysis for mupirocin resistance are repositioned in lanes 1-6 of a new rack. New test strips are positioned in lanes 1-6 of a separate rack. An additional 15 µl, of elution buffer is added to the remaining extracted nucleic acid solution in each test strip in lanes 1-6. An aliquot of 12.5 µL of the extracted nucleic acid solution is automatically pipetted to a master mix tube on the corresponding new test strip to reconstitute the master mix for the mupirocin resistance PCR analysis, using a new pipette situated on the new test strip.

The reflex PCR analysis indicates that a subset of the samples selected for the reflex test are positive for mupirocin resistance.

Example 4

Automatic Transfer of Extracted Nucleic Acid Solution to New Master Mix Tube on the Same Test Strip for Reflex PCR Analysis Sample processing and PCR analysis for MRSA are performed as described above in Example 1, with the exception that a 4-snap strip is used as shown in FIG. 2. Specifically, the 4-snap strip is configured in a similar fashion to the test strip used in Examples 1-3, but the strip comprises one additional position ("position 4") for optional placement of an additional master mix tube. For each of the 6 samples identified for reflex analysis for mupirocin resistance, an additional 15 µL of elution buffer is added to the remaining extracted nucleic acid solution in each test strip. The user places a master mix for mupirocin resistance PCR analysis in position 4 of each of the 6 test strips identified for reflex analysis. An aliquot of 12.5 µL of the extracted nucleic acid solution is automatically pipetted to the master mix tube at position 4 to reconstitute the master mix for the mupirocin resistance PCR analysis, using a new pipette situated on the new test strip. Nucleic acid amplification is performed as described above.

The reflex PCR analysis indicates that a subset of the samples selected for the reflex test are positive for mupirocin resistance.

It is to be understood that this invention is not limited to particular embodiments described, as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which the embodiments belong. Although any methods and materials similar or equivalent to those described herein may also be used in the practice or testing of the embodiments, the preferred methods and materials are now described.

The term "comprising" as used herein is synonymous with "including," "containing," or "characterized by," and is inclusive or open-ended and does not exclude additional, unrecited elements or method steps.

It must be noted that as used herein and in the appended claims, the singular forms "a," "and," and "the" include plural referents unless the context clearly dictates otherwise. Thus, for example, reference to "a method" includes a plurality of such methods and equivalents thereof known to those skilled in the art, and so forth.

All references cited herein including, but not limited to, published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium may be coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

What is claimed is:

1. A method of performing an automated assay on a plurality of specimens, said method comprising:
providing an automated instrument configured to receive and process a plurality of samples from said plurality of specimens for one or more target analytes according to one or more respective assay workflows;
receiving, at a dock located within the automated instrument, a test strip carrier including a plurality of samples to be tested;
automatically transferring, via the automated instrument, a first portion of each of said plurality of samples to be tested to a respective plurality of first vessels that comprise first reagents for a first test for a first target analyte, wherein, for each sample in said plurality of samples, said sample and said first vessel comprising the first reagents for the first test of said sample are located on a first test strip, and each test strip being located at a first position within the test strip carrier;
automatically adjusting the automated instrument according to a first assay workflow to automatically perform the first test on the first portion of said plurality of samples, the first test providing a result indicating a presence of the first target analyte in a subset of samples from the plurality of samples;
selecting, via the automated instrument, the subset of samples from the plurality of samples;
scanning, via a code reader included in the automated instrument, indicia affixed to the test strips associated with the subset of samples;
storing, in memory included in the automated instrument, assay-specific data for the subset of samples;
moving the test strips associated with the subset of samples to a second position within the automated instrument;
scanning, via the code reader, an indicator affixed to each of the test strips associated with the subset of samples;
identifying respective second positions for the test strips associated with the subset of samples based at least in part on the indicator and the assay-specific data stored in the memory;
automatically transferring, via the automated instrument, a second portion of the selected subset of samples to a second vessel comprising second reagents for a second test to determine a presence of a second target analyte according to a second assay workflow, wherein the first target analyte indicates presence of an organism in a specimen, wherein the second target analyte indicates a property of the organism in the specimen, and wherein the first target analyte is different than the second target analyte; and
automatically performing, via the automated instrument, the second test on the second portion of the selected subset of samples, the second test providing a result indicating, for an individual sample included in the second portion of the selected subset of samples, a presence of the second target analyte in the individual sample.

2. The method of claim 1, wherein each of the plurality of samples comprises a pre-processed solution of isolated nucleic acids from a respective plurality of specimens.

3. The method of claim 2, wherein the automated instrument automatically processes the plurality of specimens to obtain the respective plurality of samples comprising isolated nucleic acids.

4. The method of claim 1, wherein the second vessel comprising the second reagents for the second test is located on a second test strip.

5. The method of claim 4, wherein said second test strip comprises at least one pipette tip.

6. The method of claim 4, wherein said method comprises, prior to automatically transferring the second portion of a sample included in the selected subset of samples, adding additional liquid to a third vessel containing said sample, wherein the third vessel is located on the first test strip.

7. The method of claim 6 further comprising:
determining an amount of the additional liquid based on a first volume of the first portion and a volume of the second portion required for the second test,
wherein adding the additional liquid to the third vessel comprises pipetting the amount of the additional liquid from a fourth vessel on the first strip, and
wherein the additional liquid comprises at least one of a wash buffer or a nucleic acid elution buffer.

8. The method of claim 7, further comprising, prior to transferring the second portion, washing a pipette tip used for the first test with the additional liquid in the fourth vessel.

9. The method of claim 1, wherein, for each sample, said sample, said first vessel, and a receptacle for said second vessel are located on a single test strip.

10. The method of claim 9, wherein said method comprises, prior to transferring the subset of samples:
identifying the first test strips that include the subset of samples for testing for the second analyte; and
for each test strip that includes at least one of the subset of samples, providing the second vessel comprising the second reagents for the second test in the receptacle.

11. The method of claim 9, wherein said method comprises, prior to automatically transferring the second portion of a sample included in the selected subset of samples, providing a pipette tip configured to transfer said second portion of the sample to the second vessel comprising the second reagents for the second test.

12. The method of claim 11, wherein said pipette tip is an unused pipette tip.

13. The method of claim 11, wherein said pipette tip is a washed pipette tip.

14. The method of claim 9, wherein said method comprises, prior to automatically transferring the second portion of a sample included in the selected subset of samples, adding additional liquid to said sample.

15. The method of claim 1, wherein said first or said second test comprises a reaction selected from the group selected from: Polymerase Chain Reaction (PCR), Transcription Mediated Amplification (TMA), Oligonucleotide Ligation Assay (OLA), Ligase Chain Reaction (LCR), Rolling Circle Amplification (RCA), Strand Displacement Amplification (SDA), and a hybridization reaction.

16. The method of claim 1, wherein said method further comprises, prior to automatically transferring the second portion of a sample included in the selected subset of samples:
scanning, via the code reader, a code affixed to the second vessel, wherein the code provides identifying information regarding the second reagents; and
determining, based at least in part on the identifying information, that the second reagents are for detection of the presence of the second target analyte.

17. The method of claim 1, wherein the first test comprises a test for the simultaneous detection of methicillin resistant *Staphylococcus aureus* and *Staphylococcus aureus*, and wherein the property indicated by the second target analyte is mupirocin resistance.

18. The method of claim 17, wherein the second test comprises testing for a determinant for mupirocin resistance comprising a mupA gene.

19. A method of performing reflex testing on a plurality of specimens, said method comprising:
under control of an automated instrument:
receiving, at a dock located within the automated instrument, a test strip carrier including a plurality of specimens to be tested;
processing the plurality of specimens according to a first assay workflow to obtain a respective plurality of samples;
transferring a first portion of each of said plurality of samples to be tested to a respective plurality of first vessels that comprise first reagents for a first test for a first target analyte, the first test identified by the first assay workflow, wherein, for each sample in said plurality of samples, said sample and said first vessel comprising the first reagents for the first test of said sample are located on a first test strip, and each test strip being located at a location within the test strip carrier;
automatically adjusting the automated instrument based at least in part on the first assay workflow to perform the first test on the first portion of said plurality of samples, the first test providing a result indicating a presence of the first target analyte in a subset of samples from said plurality of samples;
selecting the subset of samples from the plurality of samples;
scanning, via a code reader included in the automated instrument, indicia affixed to the test strips associated with the subset of samples;
storing, in memory included in the automated instrument, assay-specific data for the subset of samples;
moving the test strips associated with the subset of samples to a new location within the test strip carrier;
scanning, via the code reader, an indicator affixed to each of the test strips associated with the subset of samples;
identifying the new locations for each of the test strips based at least in part on the indicator and the assay-specific data stored in the memory;
transferring a second portion of the selected subset of samples to a second vessel comprising second reagents for a second test to determine a presence of a second target analyte according to a second assay workflow, wherein the first target analyte indicates presence of an organism in a specimen, wherein the second target analyte indicates a property of the organism in the specimen, and wherein the first target analyte is different than the second target analyte; and
automatically adjusting the automated instrument based at least in part on the second assay workflow to perform the second test on the second portion of the selected subset of samples, the second test providing a result indicating, for an individual sample included in the second portion of the selected subset of samples, a presence of the second target analyte in the individual sample.

20. A method of performing reflex testing on a specimen, said method comprising:
under control of an automated instrument:
receiving, at a dock located within the automated instrument, a first test strip carrier including a specimen to be tested;

lysing cells in said specimen to obtain a sample, said sample comprising at least one isolated nucleic acid;

transferring a first portion of said sample to be tested to a first vessel comprising first reagents for a first test for a first target nucleic acid, the first test identified by a first assay workflow, wherein said sample and said first vessel are located on a first test strip, and wherein the first test strip is located at a first position within the first test strip carrier;

automatically adjusting the automated instrument based at least in part on the first assay workflow to perform said first test on said first portion of said sample, the first test providing a result indicating a presence of the first target nucleic acid in the first portion of said sample;

determining the result indicates the presence of the first target nucleic acid;

scanning, via a code reader included in the automated instrument, an indicator affixed to the first test strip;

storing, in memory included in the automated instrument, assay-specific data for said sample;

moving the first test strip associated with the subset of samples to a second position within a second test strip carrier;

receiving, at the dock, the second test strip carrier;

scanning, via the code reader, the indicator affixed to the first test strip;

identifying the second position for the first test strip based at least in part on the indicator and the assay-specific data stored in the memory;

transferring a second portion of said sample to a second vessel comprising second reagents for a second test to determine a presence of a second target nucleic acid according to a second assay workflow, wherein the first target nucleic acid indicates presence of an organism in the specimen, wherein the second target nucleic acid indicates a property of the organism in the specimen, wherein the first target nucleic acid is different than the second target nucleic acid, and wherein the second test is different than the first test; and automatically adjusting the automated instrument based at least in part on the second workflow to perform said second test on said second portion of said sample, the second test providing a result indicating a presence of the second target nucleic acid in said sample.

21. The method of claim 20, wherein the first test comprises a test for the simultaneous detection of methicillin resistant *Staphylococcus aureus* and *Staphylococcus aureus*, and wherein the property indicated by the second target nucleic acid is mupirocin resistance.

22. The method of claim 21, wherein the second test comprises testing for a determinant for mupirocin resistance comprising a mupA gene.

23. The method of claim 20 further comprises, prior to transferring the second portion of said sample to the second vessel included in the selected subset of samples:

scanning, via the code reader, a code affixed to the second vessel, wherein the code provides identifying information regarding the second reagents; and determining, based at least in part on the identifying information, that the second reagents are for detection of the presence of the second target nucleic acid.

24. A system for performing an automated assay on a plurality of samples from a respective plurality of specimen, said system comprising:

an automated instrument configured to receive and process a plurality of samples according to one or more assay workflows; said automated instrument comprising:

a dock located within the automated instrument for receiving a test strip carrier including the plurality of samples to be tested, and a code reader;

a processor; and an information storage capacity storing instructions for performing an automated assay, wherein the instructions, when executed by the processor, cause the system to:

automatically transfer, via the automated instrument, a first portion of each of said plurality of samples to be tested to a respective plurality of first vessels that comprise first reagents for a first test for a first target analyte, wherein, for each sample in said plurality of samples, said sample and said first vessel comprising the first reagents for the first test of said sample are located on a first test strip, and each test strip being located at a first position within the test strip carrier;

automatically adjust the automated instrument according to a first assay workflow to automatically perform the first test on the first portion of said plurality of samples, the first test providing a result indicating a presence of the first target analyte in a subset of samples from the plurality of samples;

select, via the automated instrument, the subset of samples from the plurality of samples;

scan, via the code reader, indicia affixed to the test strips associated with the subset of samples;

store, in memory included in the automated instrument, assay-specific data for the subset of samples;

move the test strips associated with the subset of samples to a second position within the automated instrument;

scan, via the code reader, an indicator affixed to each of the test strips associated with the subset of samples;

identify respective second positions for the test strips associated with the subset of samples based at least in part on the indicator and the assay-specific data stored in the memory;

automatically transfer, via the automated instrument, a second portion of the selected subset of samples to a second vessel comprising second reagents for a second test to determine a presence of a second target analyte according to a second assay workflow, wherein the first target analyte indicates presence of an organism in a specimen, wherein the second target analyte indicates a property of the organism in the specimen, and wherein the first target analyte is different than the second target analyte; and automatically perform, via the automated instrument, the second test on the second portion of the selected subset of samples, the second test providing a result indicating, for an individual sample included in the second portion of the selected subset of samples, a presence of the second target analyte in the individual sample.

25. The system of claim 24, wherein, for each sample, said sample, said first vessel, and a receptacle for said second vessel are located on a single test strip of the plurality of test strips, wherein said information storage capacity further comprises instructions that, when executed by the processor, cause the system to perform the steps of:

identifying a subset of said plurality of test strips for testing for the second analyte; and for each test strip in said subset, providing a corresponding second vessel comprising reagents for the second test in the receptacle.

* * * * *